(12) United States Patent
Jackson et al.

(10) Patent No.: US 12,070,249 B2
(45) Date of Patent: Aug. 27, 2024

(54) PIVOTAL BONE ANCHOR ASSEMBLY WITH BOTTOM LOADED SHANK HEAD ENGAGING RETAINER AND CLOSURE ENGAGING INSERT

(71) Applicant: Roger P. Jackson, Prairie Village, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 0 days.

(21) Appl. No.: 17/897,990

(22) Filed: Aug. 29, 2022

(65) Prior Publication Data

US 2022/0409245 A1  Dec. 29, 2022

Related U.S. Application Data

(63) Continuation of application No. 17/473,580, filed on Sep. 13, 2021, now Pat. No. 11,426,208, which is a continuation of application No. 16/685,695, filed on Nov. 15, 2019, now Pat. No. 11,116,547, which is a continuation of application No. 16/118,079, filed on Aug. 30, 2018, now Pat. No. 10,478,229, which is a continuation of application No. 14/730,981, filed on Jun. 4, 2015, now Pat. No. 10,064,658.

(60) Provisional application No. 62/007,623, filed on Jun. 4, 2014.

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/864* (2013.01)

(58) Field of Classification Search
CPC ................................. A61B 17/7032–17/7037
See application file for complete search history.

(56) References Cited

U.S. PATENT DOCUMENTS

| | | | |
|---|---|---|---|
| 5,669,911 | A | 9/1997 | Errico et al. |
| 5,672,176 | A | 9/1997 | Biedermann et al. |
| 5,690,630 | A | 11/1997 | Errico et al. |
| 5,782,833 | A | 7/1998 | Haider |
| 5,797,911 | A | 8/1998 | Sherman et al. |
| 5,885,286 | A | 3/1999 | Sherman et al. |

(Continued)

FOREIGN PATENT DOCUMENTS

| | | |
|---|---|---|
| DE | 102013204726 | 9/2014 |
| EP | 1857064 | 11/2007 |
| WO | WO 2009/055747 | 4/2009 |

OTHER PUBLICATIONS

U.S. Appl. No. 16/745,994, filed Jan. 17, 2020, Jackson.

(Continued)

*Primary Examiner* — Julianna N Harvey
(74) *Attorney, Agent, or Firm* — Polsinelli PC

(57) ABSTRACT

A polyaxial bone anchor with a receiver, a shank, a pressure insert, a retainer for holding the shank in the receiver, and a closure. The receiver includes at least one insert alignment surface formed in an axial bore of the receiver to prevent the insert from axially rotating relative to the receiver when the insert is engaged by the closure. In one aspect the retainer is uploadable through the bottom opening of the receiver, and in another aspect the insert and the retainer are both uploadable through the bottom opening.

20 Claims, 10 Drawing Sheets

(56) References Cited

U.S. PATENT DOCUMENTS

| | | | |
|---|---|---|---|
| 6,010,503 A | 1/2000 | Richelsoph et al. |
| 6,063,090 A | 5/2000 | Schläpfer |
| 6,090,111 A | 7/2000 | Nichols |
| 6,146,383 A | 11/2000 | Studer et al. |
| 6,254,602 B1 | 7/2001 | Justis |
| 6,280,442 B1 | 8/2001 | Barker et al. |
| 6,355,040 B1 | 3/2002 | Richelsoph et al. |
| 6,471,705 B1 | 10/2002 | Biedermann et al. |
| 6,485,491 B1 | 11/2002 | Farris et al. |
| 6,485,494 B1 | 11/2002 | Haider |
| 6,540,748 B2 | 4/2003 | Lombardo |
| 6,565,565 B1 | 5/2003 | Yuan et al. |
| 6,626,908 B2 | 9/2003 | Cooper et al. |
| 6,740,086 B2 | 5/2004 | Richelsoph |
| 6,835,196 B2 | 12/2004 | Biedermann et al. |
| 6,837,889 B2 | 1/2005 | Shluzas |
| 6,905,500 B2 | 6/2005 | Jeon et al. |
| 6,945,975 B2 | 9/2005 | Dalton |
| 7,066,937 B2 | 6/2006 | Shluzas |
| 7,087,057 B2 | 8/2006 | Konieczynski et al. |
| 7,141,051 B2 | 11/2006 | Janowski et al. |
| 7,144,396 B2 | 12/2006 | Shluzas |
| 7,163,539 B2 | 1/2007 | Abdelgany et al. |
| 7,186,255 B2 | 3/2007 | Baynham et al. |
| 7,264,621 B2 | 9/2007 | Coates et al. |
| 7,306,606 B2 | 12/2007 | Sasing |
| 7,311,712 B2 | 12/2007 | Dalton |
| 7,377,923 B2 | 5/2008 | Purcell et al. |
| 7,445,627 B2 | 11/2008 | Hawkes et al. |
| 7,479,156 B2 | 1/2009 | Lourdel et al. |
| 7,604,655 B2 | 10/2009 | Warnick |
| 7,625,396 B2 | 12/2009 | Jackson |
| 7,686,834 B2 | 3/2010 | Saint Martin |
| 7,686,835 B2 | 3/2010 | Warnick |
| 7,695,497 B2 | 4/2010 | Cordaro et al. |
| 7,766,915 B2 | 8/2010 | Jackson |
| 7,766,945 B2 | 8/2010 | Nilsson et al. |
| 7,776,067 B2 | 8/2010 | Jackson |
| 7,789,896 B2 | 9/2010 | Jackson |
| 7,789,900 B2 | 9/2010 | Levy et al. |
| 7,811,310 B2 | 10/2010 | Baker et al. |
| 7,833,250 B2 | 11/2010 | Jackson |
| 7,833,251 B1 | 11/2010 | Ahlgren et al. |
| 7,842,073 B2 | 11/2010 | Richelsoph et al. |
| 7,875,065 B2 | 1/2011 | Jackson |
| 7,901,436 B2 | 3/2011 | Baccelli |
| 7,909,830 B2 | 3/2011 | Frigg et al. |
| 7,914,536 B2 | 3/2011 | MacDonald et al. |
| 7,942,909 B2 | 5/2011 | Hammill, Sr. et al. |
| 7,947,065 B2 | 5/2011 | Hammill, Sr. et al. |
| 7,951,173 B2 | 5/2011 | Hammill, Sr. et al. |
| 7,967,850 B2 | 6/2011 | Jackson |
| 7,988,694 B2 | 8/2011 | Barrus et al. |
| 8,021,397 B2 | 9/2011 | Farris et al. |
| 8,048,112 B2 | 11/2011 | Suzuki et al. |
| 8,066,744 B2* | 11/2011 | Justis ............... A61B 17/7002 606/305 |
| 8,075,603 B2 | 12/2011 | Hammill, Sr. et al. |
| 8,083,776 B2 | 12/2011 | Alvarez |
| 8,197,517 B1 | 6/2012 | Lab et al. |
| 8,197,518 B2 | 6/2012 | Hammill, Sr. et al. |
| 8,221,472 B2 | 7/2012 | Peterson et al. |
| 8,353,932 B2 | 1/2013 | Jackson |
| 8,382,805 B2 | 2/2013 | Wang et al. |
| 8,398,683 B2 | 3/2013 | Berrevoets et al. |
| 8,439,922 B1 | 5/2013 | Arnold et al. |
| 8,449,578 B2 | 5/2013 | Keiser et al. |
| 8,556,938 B2 | 10/2013 | Jackson et al. |
| 8,562,652 B2 | 10/2013 | Biedermann et al. |
| 8,628,558 B2 | 1/2014 | Harvey et al. |
| 8,657,858 B2 | 2/2014 | Garamszegi et al. |
| 8,663,290 B2 | 3/2014 | Doubler et al. |
| 8,663,291 B2 | 3/2014 | Doubler et al. |
| 8,663,298 B2 | 3/2014 | Keyer et al. |
| 8,696,712 B2 | 4/2014 | Biedermann et al. |
| 8,876,869 B1 | 11/2014 | Schafer et al. |
| 8,882,817 B2 | 11/2014 | Jones et al. |
| 8,888,827 B2 | 11/2014 | Harper et al. |
| 8,926,671 B2 | 1/2015 | Biedermann et al. |
| 8,951,290 B2 | 2/2015 | Hammer et al. |
| 8,986,349 B1 | 3/2015 | German et al. |
| 9,044,272 B2 | 6/2015 | Shaffrey et al. |
| 9,060,814 B2 | 6/2015 | Doubler et al. |
| 9,078,705 B2 | 7/2015 | Matthis et al. |
| 9,119,674 B2 | 9/2015 | Matthis et al. |
| 9,155,567 B2 | 10/2015 | Auerbach et al. |
| 9,198,695 B2 | 12/2015 | Shluzas et al. |
| 9,254,150 B2 | 2/2016 | Biedermann et al. |
| 9,259,247 B2 | 2/2016 | Chandanson et al. |
| 9,358,047 B2 | 6/2016 | Mishra et al. |
| 9,439,680 B2 | 9/2016 | Biedermann et al. |
| 9,492,204 B2 | 11/2016 | Biedermann et al. |
| 9,526,529 B2 | 12/2016 | Charvet |
| 9,572,600 B2 | 2/2017 | Biedermann et al. |
| 9,615,858 B2 | 4/2017 | Doubler et al. |
| 9,649,134 B2 | 5/2017 | Hannen |
| 9,655,652 B2 | 5/2017 | Biedermann et al. |
| 9,707,013 B2 | 7/2017 | Rezach et al. |
| 9,724,145 B2 | 8/2017 | Spratt et al. |
| 9,763,702 B2 | 9/2017 | Schlaepfer et al. |
| 9,775,660 B2 | 10/2017 | Spratt et al. |
| 9,924,975 B2 | 3/2018 | Jackson et al. |
| 10,028,770 B2* | 7/2018 | Rezach ............... A61B 17/7037 |
| 10,039,572 B2 | 8/2018 | Harris et al. |
| 10,058,354 B2 | 8/2018 | Jackson et al. |
| 10,064,657 B2 | 9/2018 | Spitler |
| 10,064,658 B2 | 9/2018 | Jackson et al. |
| 10,117,680 B2 | 11/2018 | Trautwein et al. |
| 10,154,859 B2 | 12/2018 | Keyer et al. |
| 10,172,647 B2 | 1/2019 | Elsbury |
| 10,188,432 B2 | 1/2019 | Jackson et al. |
| 10,335,200 B2 | 7/2019 | Jackson |
| 10,335,203 B2 | 7/2019 | Fiechter et al. |
| 10,335,204 B2 | 7/2019 | Matthis et al. |
| 10,363,070 B2 | 7/2019 | Jackson et al. |
| 10,463,402 B2 | 11/2019 | Biester et al. |
| 10,485,594 B2 | 11/2019 | Toon et al. |
| 10,507,043 B1 | 12/2019 | Gladieux |
| 10,517,645 B2 | 12/2019 | van der Pol |
| 10,561,444 B2 | 2/2020 | Jackson |
| 10,695,100 B2 | 6/2020 | May et al. |
| 10,765,455 B2 | 9/2020 | Jackson et al. |
| 10,792,074 B2 | 10/2020 | Jackson |
| 11,051,856 B2 | 7/2021 | Jackson |
| 11,234,745 B2 | 2/2022 | Jackson |
| 2003/0149431 A1 | 8/2003 | Varieur |
| 2004/0138662 A1* | 7/2004 | Landry ............... A61B 17/861 606/279 |
| 2005/0203516 A1 | 9/2005 | Biedermann et al. |
| 2006/0058788 A1 | 3/2006 | Hammer et al. |
| 2006/0161152 A1 | 7/2006 | Ensign et al. |
| 2006/0217716 A1 | 9/2006 | Baker et al. |
| 2007/0055241 A1* | 3/2007 | Matthis ............... A61B 17/7032 606/267 |
| 2007/0118123 A1 | 5/2007 | Strausbaugh et al. |
| 2007/0208344 A1* | 9/2007 | Young ............... A61B 17/7032 623/17.16 |
| 2007/0270807 A1 | 11/2007 | Armstrong et al. |
| 2007/0270813 A1 | 11/2007 | Garamszegi |
| 2010/0137918 A1* | 6/2010 | Wilcox ............... A61B 17/863 606/301 |
| 2010/0152787 A1 | 6/2010 | Walsh et al. |
| 2011/0098755 A1* | 4/2011 | Jackson ............... A61B 17/8685 606/305 |
| 2011/0270321 A1* | 11/2011 | Prevost ............... A61B 17/7031 606/305 |
| 2012/0109208 A1* | 5/2012 | Justis ............... A61B 17/8863 606/264 |
| 2013/0218213 A1* | 8/2013 | Lemoine ............... A61B 17/7032 606/305 |
| 2014/0025119 A1 | 1/2014 | Biedermann et al. |

(56) References Cited

U.S. PATENT DOCUMENTS

| | | | | |
|---|---|---|---|---|
| 2016/0220277 A1* | 8/2016 | Rezach | ............... | A61B 17/7038 |
| 2019/0183535 A1* | 6/2019 | May | ................... | A61B 17/7032 |
| 2020/0323563 A1* | 10/2020 | Rezach | ............... | A61B 17/7034 |

OTHER PUBLICATIONS

U.S. Appl. No. 17/033,417, filed Sep. 25, 2020, Jackson.
U.S. Appl. No. 18/162,647, filed Jan. 31, 2023, Jackson.
U.S. Patent and Trademark Office, Request for Continued Examination (RCE) with Response, Mar. 22, 2024, 23 pages, U.S. Appl. No. 16/719,561.

* cited by examiner

PIVOTAL BONE ANCHOR ASSEMBLY WITH BOTTOM LOADED SHANK HEAD ENGAGING RETAINER AND CLOSURE ENGAGING INSERT

CROSS REFERENCE TO RELATED APPLICATIONS

This application is a continuation of U.S. application Ser. No. 17/473,580, filed Sep. 13, 2021, which is a continuation of U.S. application Ser. No. 16/685,695, filed Nov. 15, 2019, now U.S. Pat. No. 11,116,547, which is a continuation of U.S. application Ser. No. 16/118,079, filed Aug. 30, 2018, now U.S. Pat. No. 10,478,229, which is a continuation of U.S. application Ser. No. 14/730,981, filed Jun. 4, 2015, now U.S. Pat. No. 10,064,658, which claims the benefit of U.S. Provisional Application No. 62/007,623, filed Jun. 4, 2014, each of which is incorporated by reference in its entirety herein, and for all purposes.

BACKGROUND OF THE INVENTION

Polyaxial bone screws and related anchors of various types have been used for supporting rods and other elongate members in spinal surgery. Some of these bone screws utilize a lower pressure insert to transfer locking forces from a rod or other structure above the insert to a shank below the insert, so as to lock the shank in a fixed angular configuration with respect to a receiver. A problem encountered with the insert is that during assembly of the insert into the receiver and/or during transport and/or during implantation of the anchor into a patient, the insert may undesirably rotate from a preferred alignment and configuration relative to the receiver.

SUMMARY OF THE INVENTION

A bone anchor assembly, especially a bone screw, includes a shank for implanting into a bone, a receiver for holding the shank and receiving an elongate connecting member such as a rod, a pressure insert with opposed upwardly extending arms and a closure. Preferably, the shank has a spherical head and polyaxially joins with the receiver and is held in the receiver by a retainer that may be joined to the receiver or the shank head. The receiver has upper arms that are spaced and form a channel for receiving the elongate member. The receiver arms include break-off extensions, although in some embodiments no extensions will be included. The closure is advancingly received between the arms and applies locking pressure to the elongate member which in turn applies the pressure to the insert that locks the position of the shank relative to the receiver. The closure can also be configured to apply locking pressure to the insert before independently applying locking pressure to the elongate member.

The insert is preferably uploaded into the receiver, but may be downloaded through the channel in certain embodiments. The insert has a plurality of and particularly four opposed generally vertically aligned corners or shoulders. The receiver has a plurality of and particularly four alignment and positioning guides that form regions for receiving the insert shoulders and that snugly slidingly mate with the shoulders on the insert as the insert is being axially or vertically loaded into the receiver. The insert shoulders and the receiver guides cooperate to properly position the insert in the receiver while preventing the insert from rotating axially relative to the receiver. The insert has upwardly extending arms form an insert channel that then aligns with a similar channel of the receiver to accept the elongate member.

Preferably, the shank is cannulated and is polyaxially moveably in the receiver during positioning and thereafter locked in place.

Figure 1:
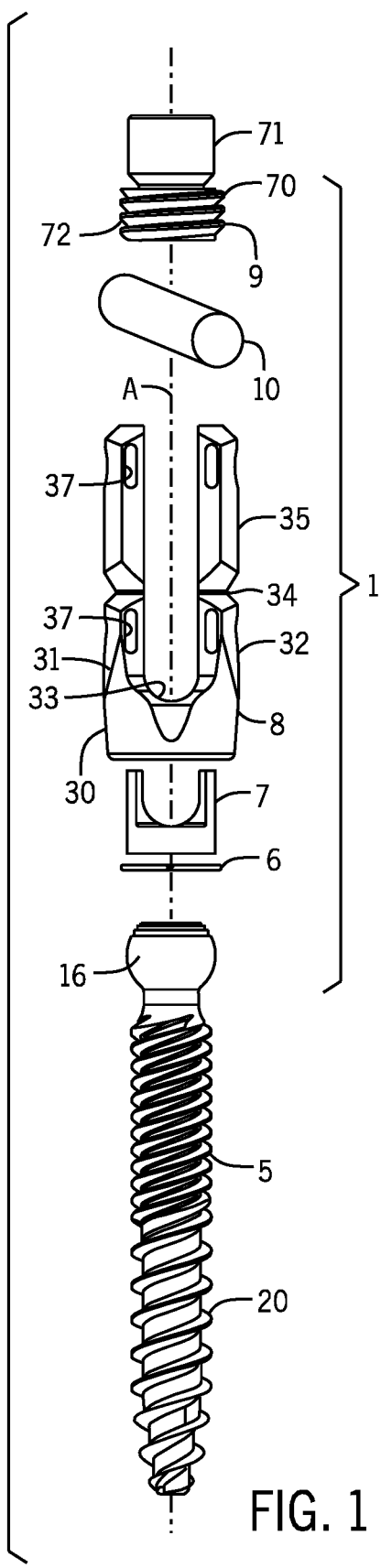
FIG. 1 is an exploded view of a bone screw including a shank, a receiver, a retainer, a pressure insert and a closure, shown in conjunction with a rod.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a bone anchor in accordance with the invention. While the illustrated anchor 1 is generally a polyaxial bone screw, it is foreseen that the invention could be utilized with other types of spinal implants that utilize pressure inserts, such as polyaxial bone hooks.

The bone anchor 1 comprises a shank 5, a retainer 6, a pressure insert 7, a receiver 8 and a closure 9 and is used with an elongate member 10.

Figure 3:
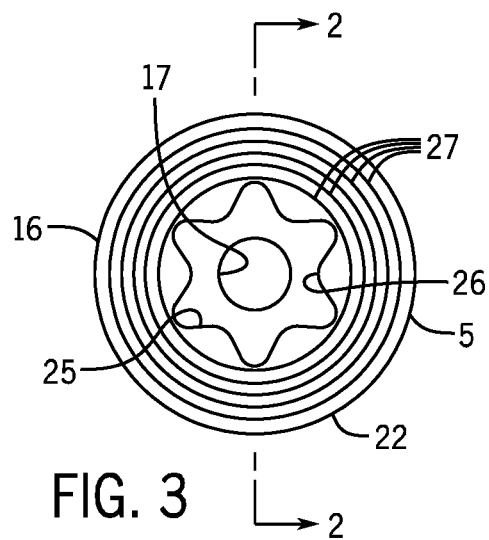
FIG. 3 is a top plan view of the bone screw.
Figure 2:
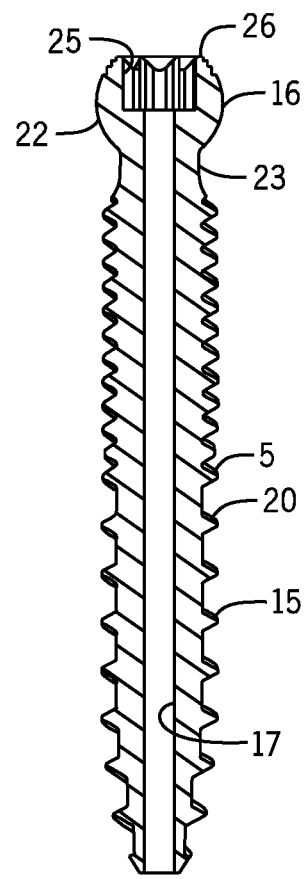
FIG. 2 is a cross sectional view of the bone screw taken along line 2-2 of FIG. 3.
Figure 4:
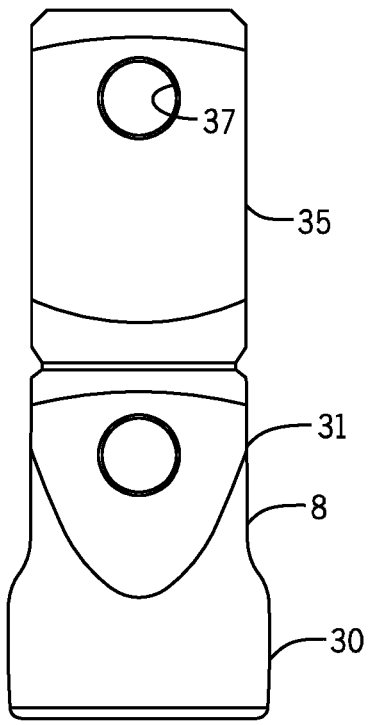
FIG. 4 is a side elevational view of the receiver.
Figure 5:
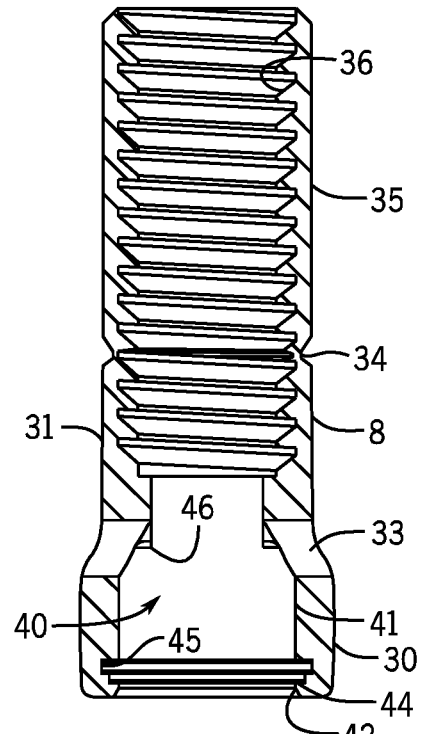
FIG. 5 is a cross sectional view of the receiver, taken along line 5-5 of FIG. 6.
Figure 6:
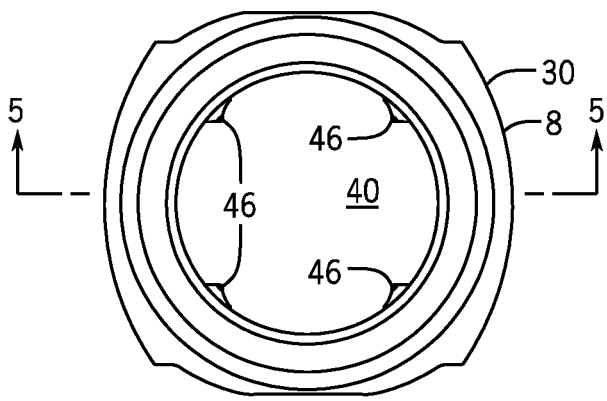
FIG. 6 is a bottom plan view of the receiver.
Figure 7:
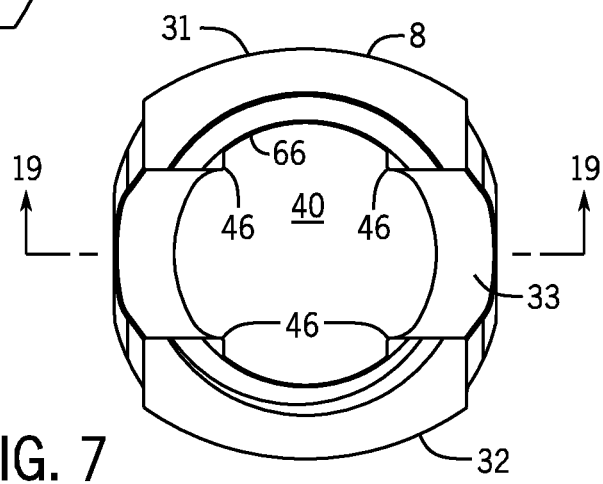
FIG. 7 is a top plan view of the receiver.
Figure 8:
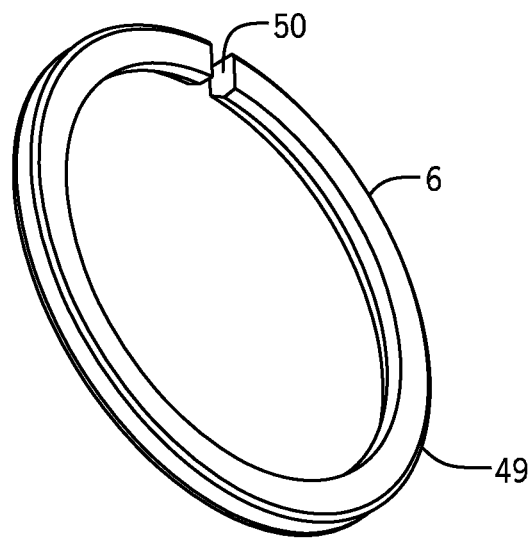
FIG. 8 is a perspective view of the retainer.
Figure 9:
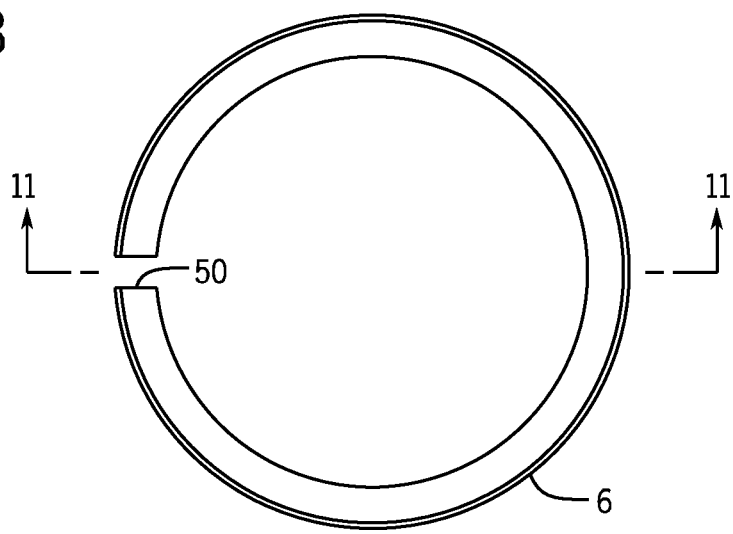
FIG. 9 is a top plan view of the retainer.
Figure 10:
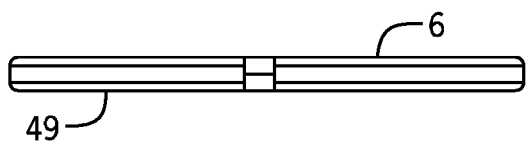
FIG. 10 is a side elevational view of the retainer.
Figure 11:
FIG. 11 is a cross sectional view of the retainer, taken along line 11-11 of FIG. 9.
Figure 12:
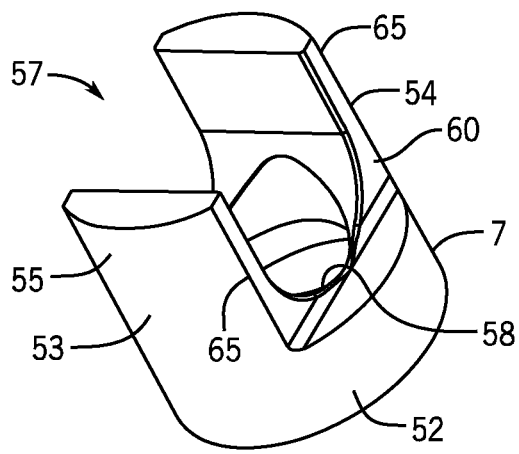
FIG. 12 is a perspective view of the insert.
Figure 13:
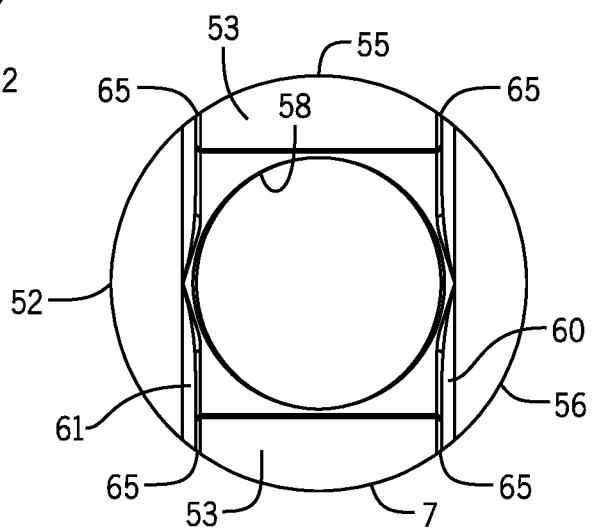
FIG. 13 is a top plan view of the insert.
Figure 14:
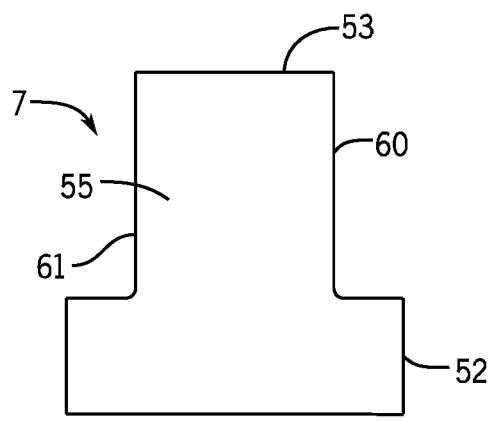
FIG. 14 is a side elevational view of the insert.
Figure 15:
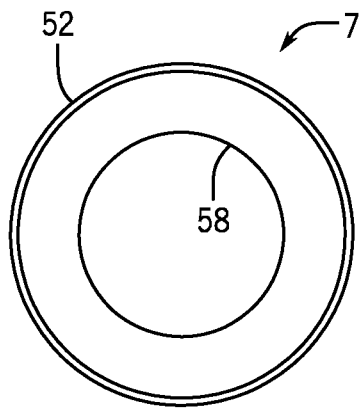
FIG. 15 is a bottom plan view of the insert.
Figure 16:
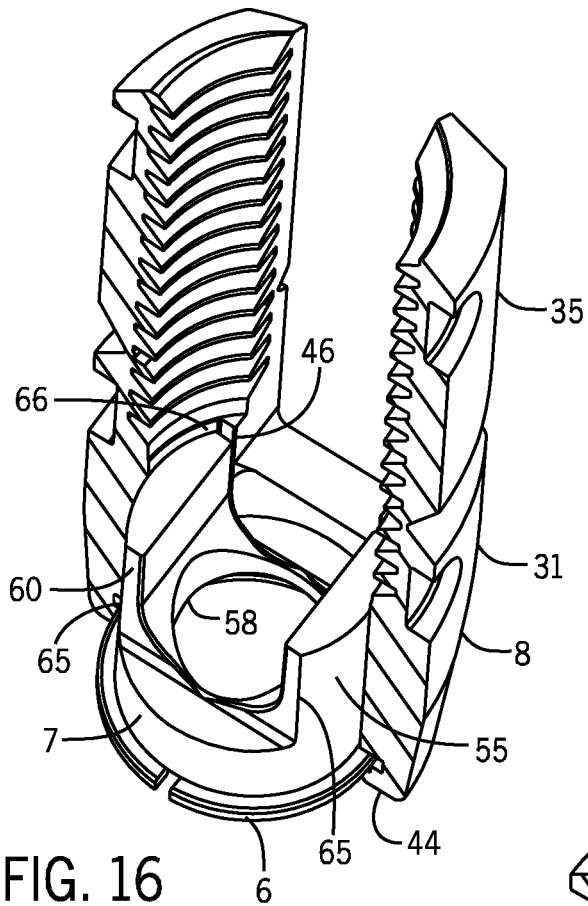
FIG. 16 is a perspective view of the receiver, insert and retainer with portions of the retainer cut away to show cooperation of the parts at a stage whereat the insert is being positioned in the receiver.
Figure 17:
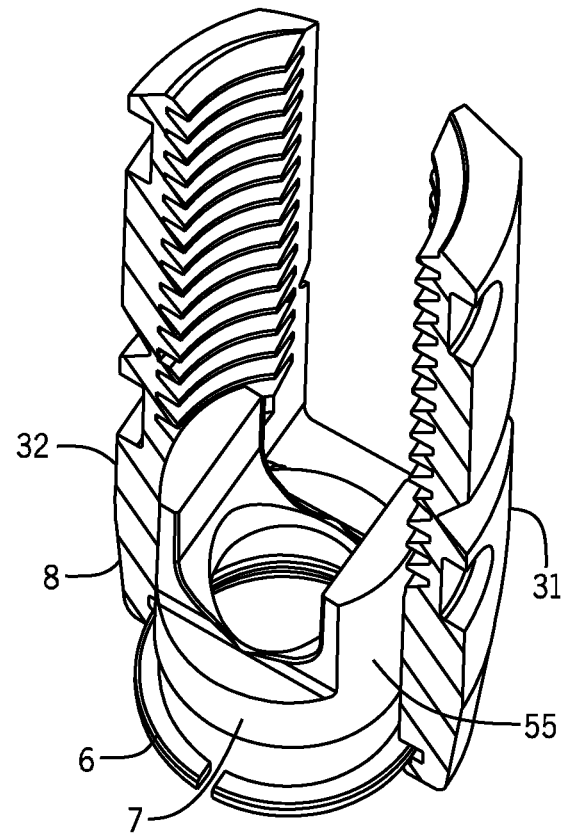
FIG. 17 is a perspective view of the receiver, insert and retainer with portions of the retainer cut away to show cooperation of the parts at a stage whereat the insert is in an upper most position relative to the receiver.
Figure 18:
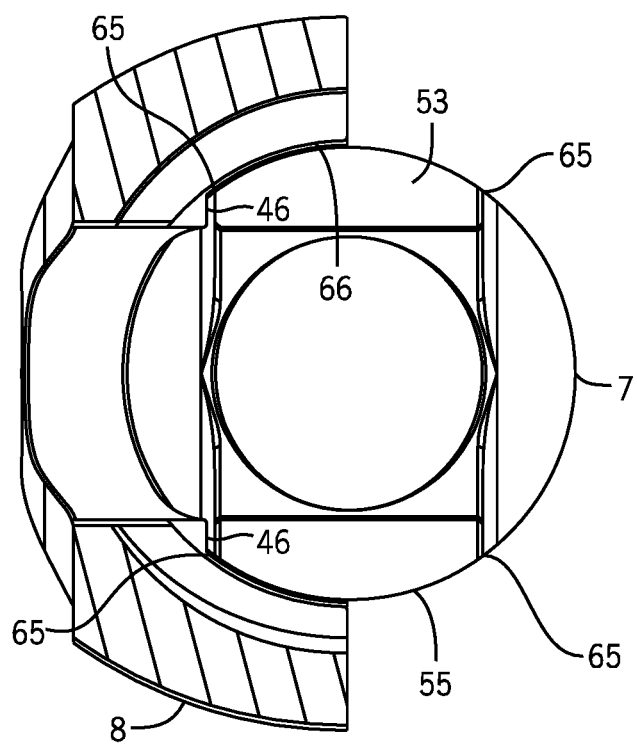
FIG. 18 is a partial top plan view of the combined receiver and insert with portions of the retainer broken away to illustrate mating of the insert and retainer.

The shank 5 as seen in FIGS. 1 to 3 has a lower portion 15 and an upper portion 16 with an axial bore 17 throughout so as to cannulate the shank 5. The lower portion 15 has a flighting or helical wound thread 20 which is doubled in the upper half for threading into a vertebra of a patient.

The shank upper portion 16 includes a bulbous and partially spherical head 22 that radially extends outward from a neck 23 joining the head 22 to the lower portion 15. Axially centered and extending downward from the top of the head 22 is a tool receiving structure 24 with radially inward extending alternating lobes 25 for receiving and gripping a tool (not shown) used to drive the shank 5 into a bone of a patient. An upper surface 26 of the head 22 has a series of concentric gripping ribs 27 for enhancing frictional contact with the insert 7 which can be made of a somewhat softer metal compared to that of the head.

Illustrated in FIGS. 4 to 7 is the receiver 8. The receiver 8 has a lower body 30 and a pair of upstanding spaced arms 31 and 32 forming an elongate member receiving channel 33. In the illustrated embodiment the channel 33 is generally U-shaped, but the shape can be varied to accommodate elongate members of different shapes. Attached by break off junctures 34 to the arms are extensions 35. On facing inner surfaces of the arms are guide and advancement structure which in the illustrated embodiment are helical wound reverse angle thread forms 36, but can be various types of threads, such as a conventional V thread, buttress or square threads or helical flanges. Tool grasping apertures 37 are located on the sides of each arm 31 and 32.

Located in the receiver body 30 is a chamber 40 formed by side walls 41 that opens both into the channel 33 above and to the exterior through a lower opening 42. During assembly of the anchor 1, the chamber 40 receives both the shank head 22 and the insert 7. The lower end of the chamber has a first groove 44 and a larger second groove 45 that are axially aligned with a central Axis A of the receiver, the purpose of which will be discussed later. It is foreseen that the shank can be downloaded into the receiver and not require a retainer, and that the receiver does not have but one groove for the retainer.

Located on the chamber side walls 41 near an upper side thereof are four spaced and radially inward projecting projections or guides 46. The guides 46 cooperate with the insert 7 as discussed below.

The retainer 6 is shown in FIGS. 8 to 11. The retainer 6 is an open resilient ring 49 with a gap or break 50 to allow contraction and expansion thereof. The ring 49 is compressed and loaded into the receiver. This can occur before or after loading the shank in some embodiments. In the embodiment shown, the ring is loaded first and passes over the shank head 22 during loading of the head 22 into the chamber 40 thereby capturing the shank. During expansion, the ring 49 is received in the larger receiver groove 45 after which the ring 49 is lowered into the smaller groove 44 which is about the same diameter as the ring 49 so that the ring 49 fits snugly therein to prevent repeated expansion. In this manner, the ring 49 holds the shank head 22 in the receiver 8 and allows the shank 5 to pivot relative to the receiver 8 during positioning and before locking.

The insert 7 is best seen in FIGS. 12 to 18. The insert 7 includes a lower body 52 with a pair of spaced upstanding arms 53 and 54. The arms 53 and 54 and body 52 have a continuous radially outer surface 55 on each side which are substantially smooth and vertically or axially aligned, but radially spaced from the Axis A. The arms 53 and 54 form a central U-shaped channel 57 therebetween and there is a central axially aligned and centered bore 58.

On either side of the arms 53 and 54 are flat surfaces 60 and 61. At the intersection of the surfaces 60 and 61 with the surfaces 55 and 56 are formed four corners or shoulders 65. The shoulders 65 extend along a length of the insert 7 and are vertically or axially aligned. Each of the shoulders 65 are sized and shaped to vertically slide, but snugly mate with the receiver guides 46. This allows the insert 7 to move vertically during loading into the receiver 8 and during certain positioning required during assembly and implantation of the anchor 1, but prevents the insert 7 from rotating about the axis A relative to the receiver 8. This relationship is perhaps best seen in FIG. 16 wherein the left rear shoulder 65 is seen sliding vertically along the receiver surface 66 and guide 46, but is constrained from axial rotation by the abutment of the shoulder 65 with the guide 46.

The closure 9 is best seen in FIG. 1. The closure 9 has a body 70 with a head 71 that has a tool engagement surface 72 and that breaks from the body 70 at a predetermined torque. Helically wound about the body 70 is a guide and advancement structure 73 which operably mates with the guide and advancement structure 36 on the receiver arms 31 and 32.

The elongate member 10 is for extending between various implants (not shown) in an overall system. The illustrated elongate member 10 is a circular rod, although members of various construction and shape may be utilized.

FIGS. 19 to 27 show various stages in the assembly and utilization of the anchor 1 in a snap-on screw embodiment.

Figure 19:
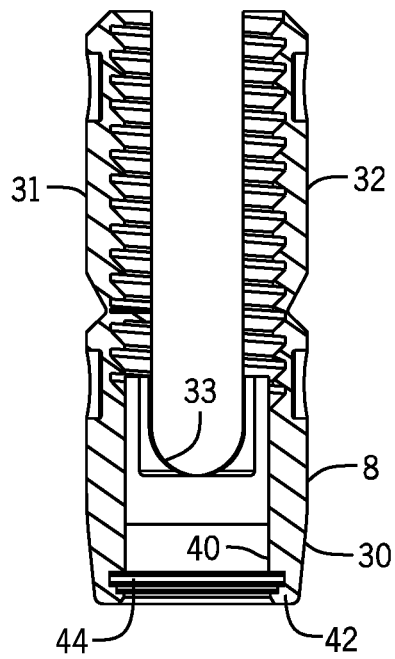
FIG. 19 is a cross section of a side elevational view of the receiver, taken along line 19-19 of FIG. 7 showing the receiver before assembly of the bone anchor.
Figure 20:
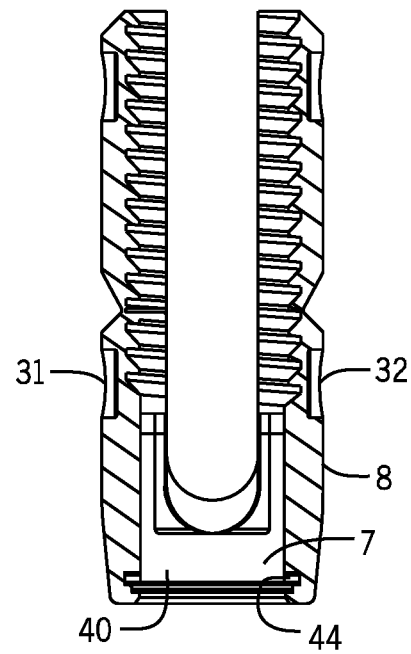
FIG. 20 is a cross section of the receiver, as in FIG. 19, showing a first stage of the positioning of the insert in the receiver.
Figure 21:
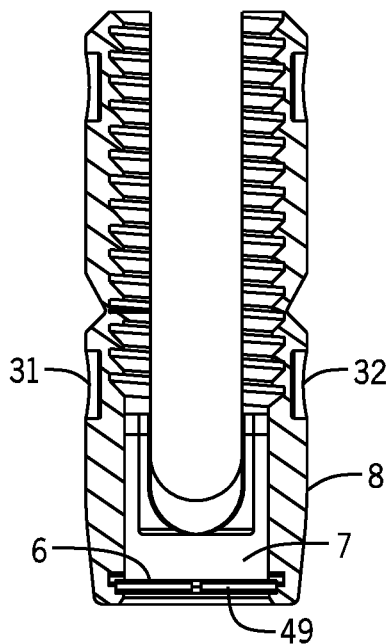
FIG. 21 is a cross section of the receiver as in FIG. 20 showing a second stage of the positioning of the retainer in the receiver.
Figure 22:
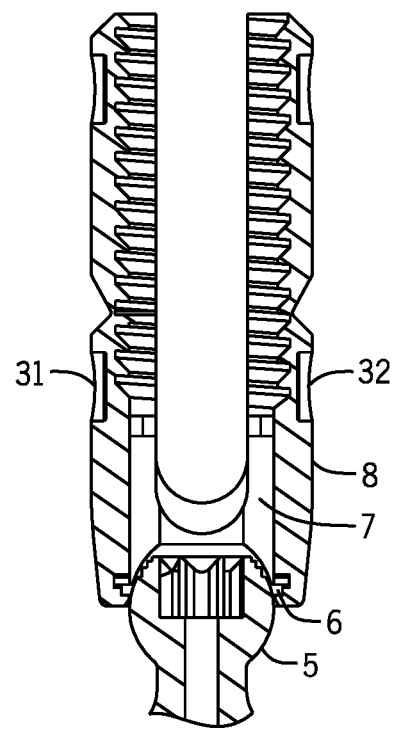
FIG. 22 is a cross section of the receiver as in FIG. 20 showing a third stage of the positioning of the shank head in the receiver with the shank first entering the receiver.

The receiver 8 is shown by itself in FIG. 19. In FIG. 20 the pressure insert 7 is uploaded through the opening 42 into the chamber 40. In FIG. 21, the retainer ring 49 is placed in the chamber 40. In FIG. 22, the top of the shank 5 is partially inserted into the chamber 40 and abuts against the retainer 6.

Figure 23:
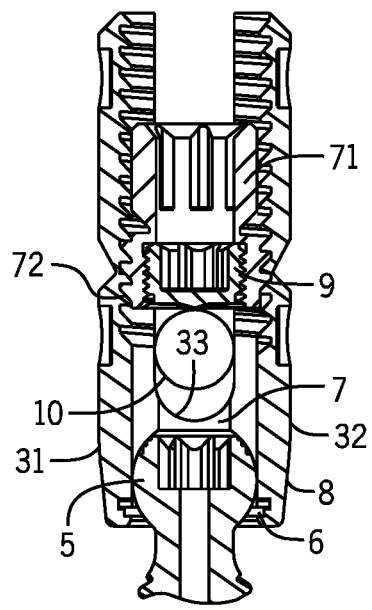
FIG. 23 is a cross section of the receiver as in FIG. 19 showing a fourth stage of the positioning of the insert in the receiver with the shank head having passed through the retainer and being captured in the receiver.
Figure 24:
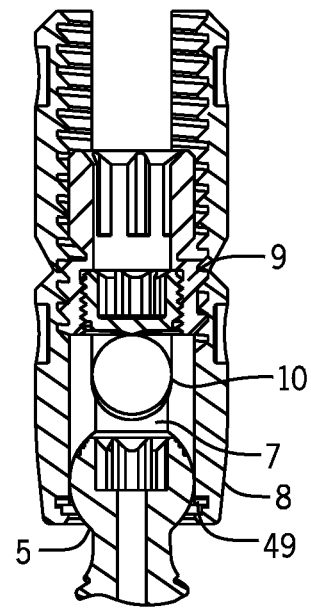
FIG. 24 is a cross section of the receiver as in FIG. 19 showing view of a fifth stage of the positioning of the insert in the receiver with a rod and closure added and the closure applying pressure only to insert.

In FIG. 23, the ring 6 has captured the shank head after moving up into the larger receiver groove 45 and coming back down into the smaller groove, while the insert moved upward being aligned and guided by the guides 46. In FIG. 24, the shank head is, again, shown fully captured and the ring 49, which is located around the lower half of the head 22, is shown fully seated in the lower and smaller groove 44. The closure is seen compressing the insert to lock the shank with respect to the receiver before locking the rod.

Figure 25:
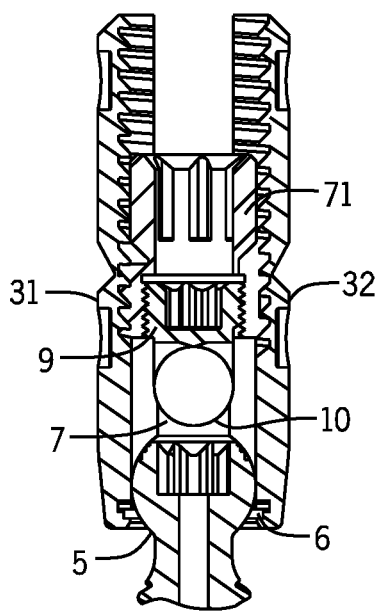
FIG. 25 is a cross section of the receiver as in FIG. 19 showing a sixth stage of the positioning of the insert in the receiver showing the closure pushing the rod downwardly into a locked position against the insert.
Figure 26:
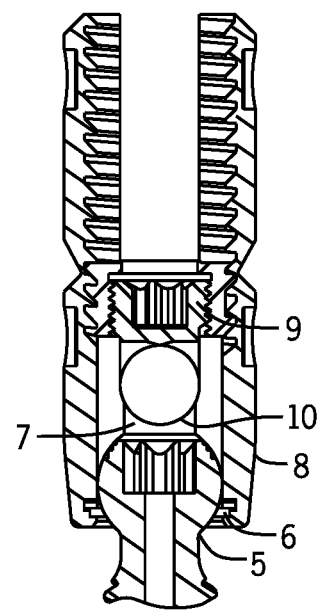
FIG. 26 is a cross section of the receiver as in FIG. 19 showing a ninth stage of the positioning of the insert in the receiver with the rod secured in place in a channel of the receiver and a head of the closure broken away.

Shown in FIG. 25, the closure is now also independently locking the rod 10. In FIG. 26, the closure 9 is fully advanced against both the insert and the rod 10 and the head 71 is broken away. The arm extensions 35 can then be broken away (not shown). At this point, the closure 9 applies pressure to the rod 10 and/or pressure insert 7 which applies pressure to the shank 5 thereby locking the shank 5 in a fixed rotational position relative to the axis A of the receiver with the shank implanted in a bone (not shown). Prior to locking the shank 5 is polyaxially rotatable relative to the receiver 8 meaning that the angle of the shank 5 may be varied with respect to the receiver 8 and the axis A.

Figure 27:
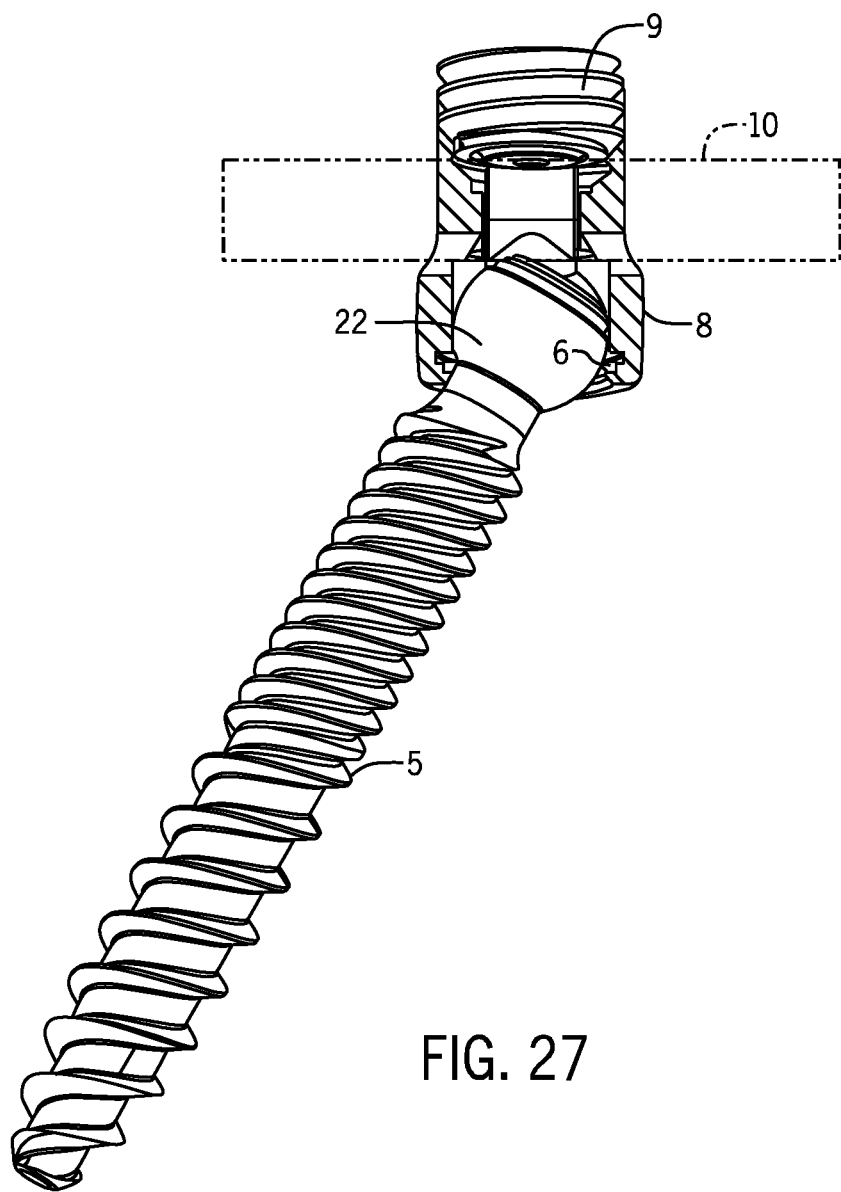
FIG. 27 is a side elevational view of the bone anchor with a rod shown in phantom and with the shank pivoted with respect to the retainer with portions removed to show detail thereof.

FIG. 27 shows an alternative locked configuration for the polyaxial positioning of the shank 5 relative to the receiver 8.

Once the insert 7 enters the receiver chamber 40, the guides 46 cooperate with the insert shoulder 65 to guide the insert 7 up and down in the receiver 8 while preventing rotation of the insert relative to the receiver 8.

Figure 28:
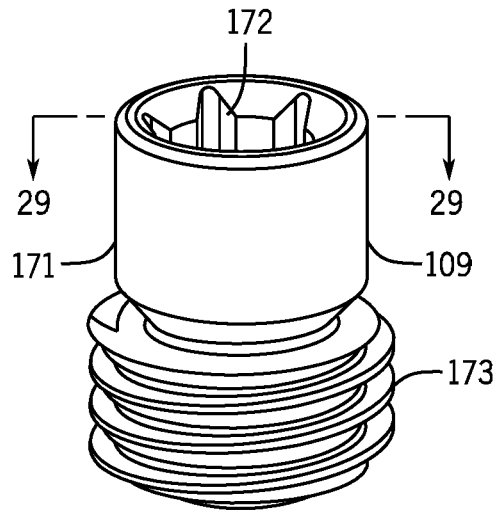
FIG. 28 is a perspective view of a second embodiment of a closure usable with the present invention.
Figure 29:
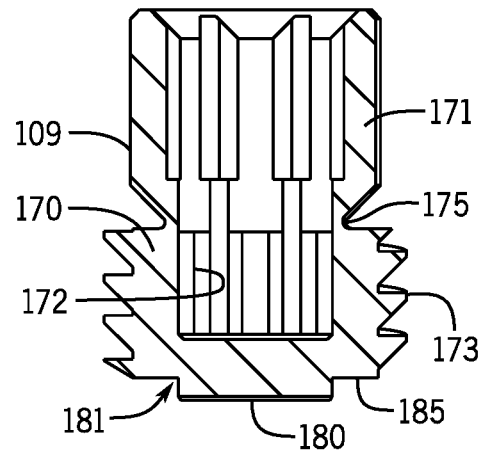
FIG. 29 is a cross sectional view of the closure of FIG. 28, taken along line 29-29 of FIG. 28.
Figure 30:
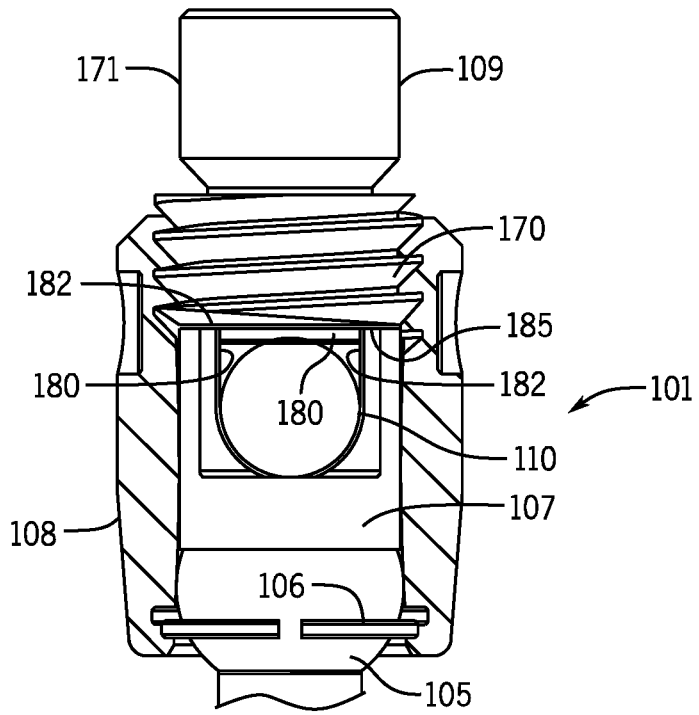
FIG. 30 is a side elevational view of a bone anchor assembly with the closure of FIG. 28 and a receiver, rod, pressure insert and retainer with the receiver partially broken away to show detail thereof.

Shown in FIGS. 28 to 30 is an alternative closure for use with the present invention generally identified by the reference numeral 109. It is shown in use in an implant assembly 101 shown in FIG. 30. The closure 109 differs in several aspects from the closure 9. In particular, the closure 9 has an outer ring with a central screw sometimes referred to as a dual innie. The present closure has a unitary body 170 and includes a break off head 171. The body 170 includes outer helical wound reverse angle threads 173 and an internal tool receiving structure 172 for driving the closure 109. The head 171 is attached to the body 170 at a break off neck 175. The head 171 is shown attached to the body 170 in FIG. 30 just prior to breaking away. Importantly, depending from the bottom of the body 170 is a solid circular ring 180 that provides a reduced radius or step down 181.

Seen in FIG. 30 is the closure 109 in a receiver 108 along with a shank 105, a shank retainer 106, a pressure insert 107 and a rod 110. The present insert 107 has two upstanding arms 180 and 181 each with a top surface 182. The arms 180 and 181 are spaced such that the ring 180 on the bottom of the closure 109 passes therebetween on assembly with a slight clearance on each side. A lower surface 185 of the closure body 170 that is radially outward of the ring 180 remains spaced from the insert arms upper surface 182 during assembly and locking. The parts of the assembly 1 and 101 and especially the receiver 8 and 108 and the insert 7 and 107 are preferably constructed of metal that is strong and resists bending or splaying of the arms of either the insert 107 or receiver 108. Preferred material of construction is any grade of titanium and most preferably, cobalt chrome.

It is to be understood that while certain forms of the present invention have been illustrated and described herein, it is not to be limited to the specific forms or arrangement of parts described and shown.

What is claimed is:

1. A pivotal bone anchor assembly for securing an elongate rod to a bone of a patient, the pivotal bone anchor assembly comprising:
    a shank having a partially spherical shank head and an anchor portion opposite the shank head configured for fixation to the bone;
    a receiver comprising a base defining a lower portion of an axial bore centered about a longitudinal axis, communicating with a bottom of the receiver through a bottom opening, and configured to receive the shank head through the bottom opening, and a first pair of upright arms extending upwardly from the base to define a first channel configured to receive the elongate rod, the axial bore extending upward through the first channel to a top of the receiver and including:
        a discontinuous guide and advancement structure adjacent the top of the receiver;
        a circumferential recess adjacent the bottom opening defined in part by an upwardly-facing seating surface; and
        longitudinally extending abutment surfaces located between the circumferential recess and the discontinuous guide and advancement structure;
    an insert having a second pair of upright arms defining a second channel configured to receive the elongate rod and a lower surface configured to engage the shank head, the insert being uploadable through the bottom opening into the axial bore prior to the shank head and slidably engageable with the abutment surfaces so as to inhibit rotation therebetween and hold the second channel of the insert in alignment with the first channel of the receiver;
    an open retainer ring having a thickness between a top surface and a bottom surface and a gap extending entirely through the thickness of the open retainer ring, the open retainer ring being compressible and uploadable into the circumferential recess of the axial bore of the receiver through the bottom opening before the shank head is received within the axial bore, the open retainer ring being configured to resiliently capture the shank head within the base of the receiver; and
    a closure top positionable within the axial bore above the insert and having a cylindrical outer side surface configured to rotatably engage with the discontinuous guide and advancement structure of the axial bore,
    wherein the second pair of upright arms of the insert are configured to extend above a top surface of the elongate rod when the elongate rod is positioned in the first and second channels and are directly engageable by a lower surface of the closure top so as to lock the shank with respect to the receiver.

2. The pivotal bone anchor assembly of claim 1, wherein the closure top is selected from the group consisting of a single piece threaded closure top and a two piece threaded closure top.

3. The pivotal bone anchor assembly of claim 1, wherein the closure top further comprises a two piece threaded closure top having an outer ring configured to engage top surfaces of the second pair of upright arms and a central screw configured to engage the elongate rod.

4. The pivotal bone anchor assembly of claim 1, wherein the shank is cannulated so as to have a central opening along an entire length thereof.

5. The pivotal bone anchor assembly of claim 1, wherein the receiver further includes at least one breakoff extension extending upwardly from the upstanding arms of the receiver.

6. The pivotal bone anchor assembly of claim 1, wherein the open retainer ring is in a non-contracted state when the bottom surface of the open retainer ring is seated against the upwardly-facing seating surface.

7. The pivotal bone anchor assembly of claim 1, wherein at least a portion of the shank head extends above the top surface of the open retainer ring when the shank head is captured within the axial bore of the receiver.

8. A pivotal bone anchor assembly for securing an elongate rod to a bone of a patient with a closure top, the pivotal bone anchor assembly comprising:
  a shank having a partially spherical shank head and an anchor portion opposite the shank head configured for fixation to the bone;
  a receiver comprising a base defining a lower portion of an axial bore centered about a longitudinal axis, communicating with the bottom of the receiver through a bottom opening, and configured to receive the shank head, and a first pair of upright arms extending upwardly above the base to define a first channel configured to receive the elongate rod, the axial bore extending upward through the first channel to a top of the receiver and including:
    a discontinuous guide and advancement structure adjacent the top of the receiver configured to engage the closure top;
    a circumferential recess adjacent the bottom opening defined in part by a seating surface; and
    longitudinally extending abutment surfaces located between the circumferential recess and the discontinuous guide and advancement structure;
  an insert having a second pair of upright arms defining a second channel configured to receive the elongate rod and a lower surface configured to engage the shank head, the insert being uploadable through the bottom opening into the axial bore prior to the shank head and slidably engageable with the abutment surfaces so as to inhibit rotation therebetween and hold the second channel of the insert in alignment with the first channel of the receiver; and
  an open retainer ring having a thickness between a top surface and a bottom surface and a gap extending entirely through the thickness of the open retainer ring, the open retainer ring being compressible and uploadable into the circumferential recess of the axial bore of the receiver through the bottom opening prior to the shank head being uploaded and received within the axial bore, the open retainer ring being configured to resiliently capture the shank head within the base of the receiver,
  wherein the second pair of upright arms are configured to extend above a top surface of the elongate rod when the elongate rod is positioned within the first and second channels, and
  wherein top surfaces of the second pair of upright arms are configured for direct engagement by a lower surface of the closure top so as to lock the shank with respect to the receiver.

9. The pivotal bone anchor assembly of claim 8 and further comprising the elongate rod and the closure top, wherein the closure top is selected from the group consisting a single piece threaded closure top or a two piece threaded closure top.

10. The pivotal bone anchor assembly of claim 9, wherein the two piece threaded closure top further comprises an outer ring configured to engage top surfaces of the second pair of upright arms and a central screw configured to engage the elongate rod.

11. The pivotal bone anchor assembly of claim 9, wherein the closure top is configured for positioning within the first channel of the receiver above the elongate rod and in engagement with the discontinuous guide and advancement structure of the axial bore to apply a downward pressure toward a top of the elongate rod, so as to secure the elongate rod to the bone of the patient.

12. The pivotal bone anchor assembly of claim 8, wherein the open retainer ring is seated against the seating surface and non-pivoting with respect to the receiver after capturing the shank head in the recess of the receiver and prior to locking the assembly with the closure top.

13. The pivotal bone anchor assembly of claim 8, wherein the receiver further includes at least one breakoff extension extending upwardly from the upstanding arms of the receiver.

14. The pivotal bone anchor assembly of claim 8, wherein at least a portion of the shank head extends above the top surface of the open retainer ring when the shank head is captured within the axial bore of the receiver.

15. A method of assembling a pivotal bone anchor assembly for securing an elongate rod to a bone of a patient with a closure top, the method comprising:
  uploading an insert through a bottom opening into an axial bore of a receiver such that the insert is slidably engaged with longitudinally extending abutment surfaces formed in the axial bore so as to inhibit rotation between the insert and receiver and hold a second channel of the insert in alignment with a first channel of the receiver, the insert including a second pair of upright arms defining the second channel configured to receive the elongate rod, and the receiver including a base and a first pair of upright arms extending upwardly above the base to define the first channel configured to receive the elongate rod, the axial bore extending upward through the first channel to a top of the receiver and including a discontinuous guide and advancement structure adjacent the top of the receiver configured to engage the closure top, the second pair of upright arms of the insert being configured to extend above the elongate rod when the elongate rod is positioned in the first and second channels and having top surfaces configured for direct engagement by a lower surface of the closure top;
  uploading an open retainer ring in a compressed condition through a bottom opening of the receiver and into a circumferential recess formed into a lower portion of the axial bore defined by the base of the receiver, the open retainer ring having a thickness between a top surface and a bottom surface and a gap extending entirely through the thickness of the open retainer ring;
  uploading a partially spherical shank head of a shank through the bottom opening and into the axial bore of the receiver subsequent to the open retainer ring having been uploaded through the bottom opening into the circumferential recess, the shank including an anchor portion opposite the shank head configured for fixation to the bone; and capturing the shank head within the base of the receiver by passing the shank head through the open retainer ring in the axial bore, the open retainer ring then resiliently contracting about the shank head within the circumferential recess with at least a portion of the shank head extending above the top surface of the open retainer ring.

16. The method of claim 15, wherein positioning the insert in the axial bore of the receiver further comprises uploading the insert into the axial bore of the receiver through the bottom opening prior to the open retainer ring so as to be at least partially slidably positionable within the first channel of the receiver.

17. The method of claim 15, wherein the insert includes a lower surface opposite the second channel, and the lower surface engages the shank head subsequent to the shank head being uploaded into the base of the receiver.

18. The method of claim 15, wherein, in the process of uploading the shank head through the bottom opening, the shank head drives the open retainer ring upwards within the axial bore to align with an expansion recess defined in the axial bore above the circumferential recess.

19. The method of claim 18, wherein, in the process of passing the shank head through the open retainer ring in the axial bore, the head expands the open retainer ring within the expansion recess.

20. The method of claim 15, further comprising:
positioning the elongate rod within the first and second channels; and
downwardly rotatably engaging a cylindrical outer side surface of the closure top with the discontinuous guide and advancement structure of the axial bore until the lower surface of the closure top directly engages the top surfaces of the second pair of upright arms of the insert so as to lock the shank with respect to the receiver.

* * * * *